(12) United States Patent
Yong et al.

(10) Patent No.: US 7,687,631 B2
(45) Date of Patent: Mar. 30, 2010

(54) SYNTHESIS OF DIETHYL{[5-(3-FLUOROPHENYL)-PYRIDINE-2YL]METHYL}PHOSPHONATE

(75) Inventors: Kelvin H. Yong, Lyndhurst, NJ (US); Ilia A. Zavialov, Princeton, NJ (US); Jianguo Yin, Plainsboro, NJ (US); Xiaoyong Fu, Edison, NJ (US); Tiruvettipuram K. Thiruvengadam, Kendall Park, NJ (US)

(73) Assignee: Schering Corporation, Kenilworth, NJ (US)

( * ) Notice: Subject to any disclaimer, the term of this patent is extended or adjusted under 35 U.S.C. 154(b) by 320 days.

(21) Appl. No.: 11/824,245

(22) Filed: Jun. 29, 2007

(65) Prior Publication Data

US 2008/0004449 A1  Jan. 3, 2008

Related U.S. Application Data

(60) Provisional application No. 60/817,867, filed on Jun. 30, 2006.

(51) Int. Cl.
C07D 405/06 (2006.01)
(52) U.S. Cl. .................................. 546/284.1
(58) Field of Classification Search ............... 546/284.1

See application file for complete search history.

(56) References Cited

U.S. PATENT DOCUMENTS

| 6,063,847 | A | 5/2000 | Chackalamannil et al. |
| 7,235,567 | B2 | 6/2007 | Wu |
| 7,541,471 | B2 * | 6/2009 | Thiruvengadam et al. ............... 546/284.1 |
| 2003/0216437 | A1 | 11/2003 | Chackalamannil et al. |
| 2004/0192753 | A1 | 9/2004 | Chackalamannil et al. |
| 2005/0267155 | A1 | 12/2005 | Chelliah et al. |
| 2006/0247450 | A1 | 11/2006 | Wu et al. |

OTHER PUBLICATIONS

International Search Report, PCT/US2007/015161; mailed Nov. 14, 2007; 4 pages. Published with a publication on Jan. 10, 2008 as W02008/005348.

* cited by examiner

*Primary Examiner*—Patricia L Morris
(74) *Attorney, Agent, or Firm*—Patent Practitioners of Schering Corp.; H. Eric Fischer

(57) ABSTRACT

This application discloses a novel process for the preparation of phosphonate esters useful as intermediates in the preparation of himbacine analogs, themselves useful as thrombin receptor antagonists. The chemistry taught herein can be exemplified by the following scheme:

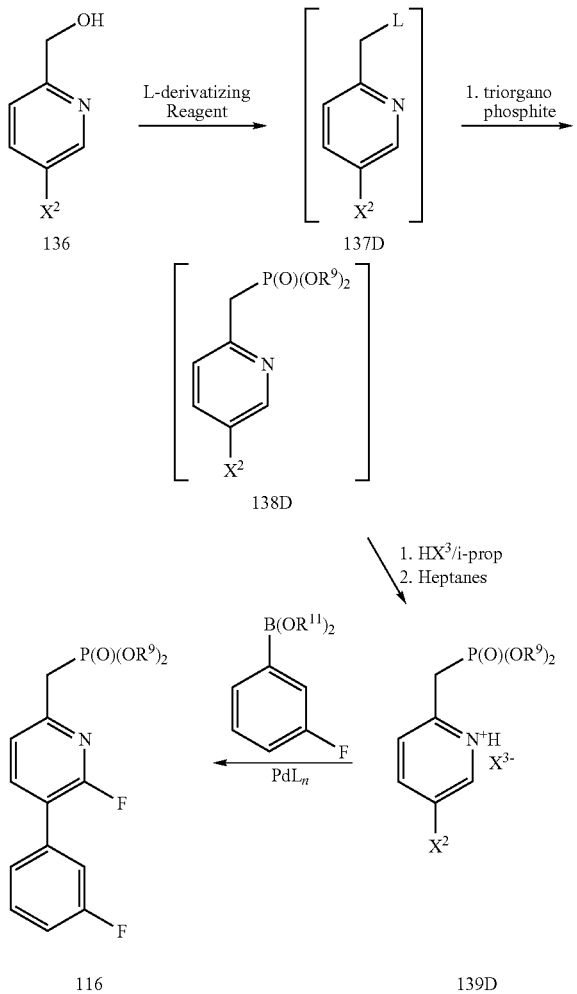

wherein $R^9$ is selected from alkyl, aryl heteroaryl and arylalkyl groups having 1 to 10 carbon atoms, and $R^{11}$ is selected independently for each occurrence from alkyl, aryl heteroaryl and arylalkyl groups having 1 to 10 carbon atoms and hydrogen, $X^2$ is Cl, Br, or I; $X^3$ is selected from Cl and Br; and $PdL_n$ is a supported palladium metal catalyst or a soluble heterogeneous palladium catalyst. The L-derivatizing reagent is a moiety which converts the alcohol functional group of compound 137D to any leaving group which can be displaced by a triorgano-phosphite phosphonating agent.

10 Claims, No Drawings

1

SYNTHESIS OF DIETHYL{[5-(3-FLUOROPHENYL)-PYRIDINE-2YL]METHYL}PHOSPHONATE

CROSS-REFERENCE TO RELATED APPLICATIONS

This application is based on and claims the priority of U.S. Provisional Application No. 60/817,867 filed Jun. 30, 2006, which is incorporated by reference herein in its entirety.

FIELD OF THE INVENTION

This application discloses a novel process in the preparation of dialkyl{[5-(3-fluorophenyl)-pyridine-2-yl]alkyl} phosphonate compounds which are useful in the synthesis of himbacine analogs, themselves useful as thrombin receptor antagonists.

BACKGROUND OF THE INVENTION

As described in copending U.S. patent application Ser. No. 11/331,324, filed Jan. 12, 2006 (herein, "the '324 application"), the disclosure of which is incorporated herein in its entirety by reference, himbacine analogs are useful as thrombin receptor antagonists. Thrombin is known to have a variety of activities in different cell types. Thrombin receptors are known to be present in such diverse cell types as human platelets, vascular smooth muscle cells, endothelial cells, and fibroblasts. Thrombin receptor antagonists may be useful in the treatment of thrombotic, inflammatory, atherosclerotic and fibroproliferative disorders, as well as other disorders in which thrombin and its receptor play a pathological role, for example, as described in U.S. Pat. No. 6,063,847, the disclosure of which is incorporated by reference. Additional examples of thrombin receptor antagonists useful in the treatment of thrombotic, inflammatory, atherosclerotic, and fibroproliferative disorders, and the synthesis of these compounds, are described in published U.S. Patent Application No. 2003/0216437 (herein, "the '437 publication"), the disclosure of which is incorporated herein in its entirety by reference.

One thrombin receptor antagonist identified is an orally bioavailable compound derived from himbacine having the structure of the compound 11:

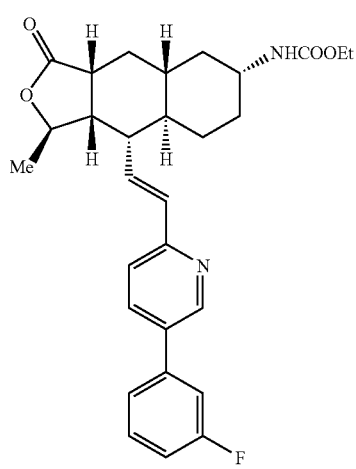

11

Processes for the synthesis of this and similar himbacine analog thrombin receptor antagonists are disclosed in U.S. Pat. No. 6,063,847, and U.S. publication no. 2003/0216437, methods of using thrombin receptor antagonists are disclosed in U.S. publication no. 2004/0192753, and the synthesis of the bisulfate salt of a particular himbacine analog is disclosed in U.S. publication no. 2004/0176418, the disclosures of which are incorporated by reference herein.

As described in the '324 application mentioned herein above, compound 11 may be synthesized from Compound 15:

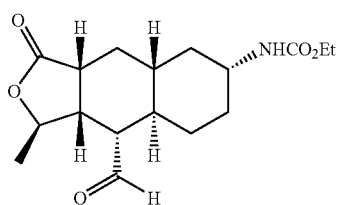

15 by treatment with compound 16 in accordance with Scheme I.

Scheme I

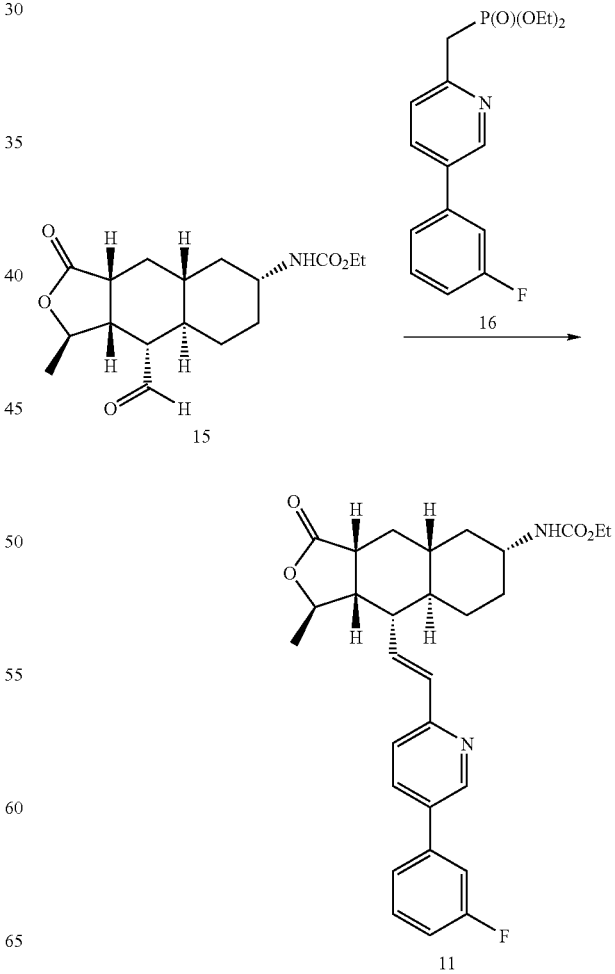

Compound 15 is in turn prepared from compound 1:

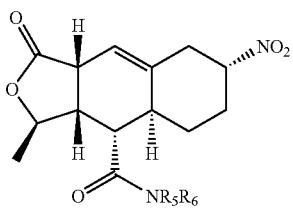

wherein $R_5$ and $R_6$ are each independently selected from the group consisting of H, alkyl, alkenyl, alkynyl, alkoxy, cycloalkyl, aryl, alkylaryl, arylalkyl, and heteroaryl groups, in four steps in accordance with the synthesis scheme shown in the copending '324 application, which synthetic schemes are incorporated herein by reference.

The copending '324 application describes the preparation of compound 16 in accordance with Scheme II, below.

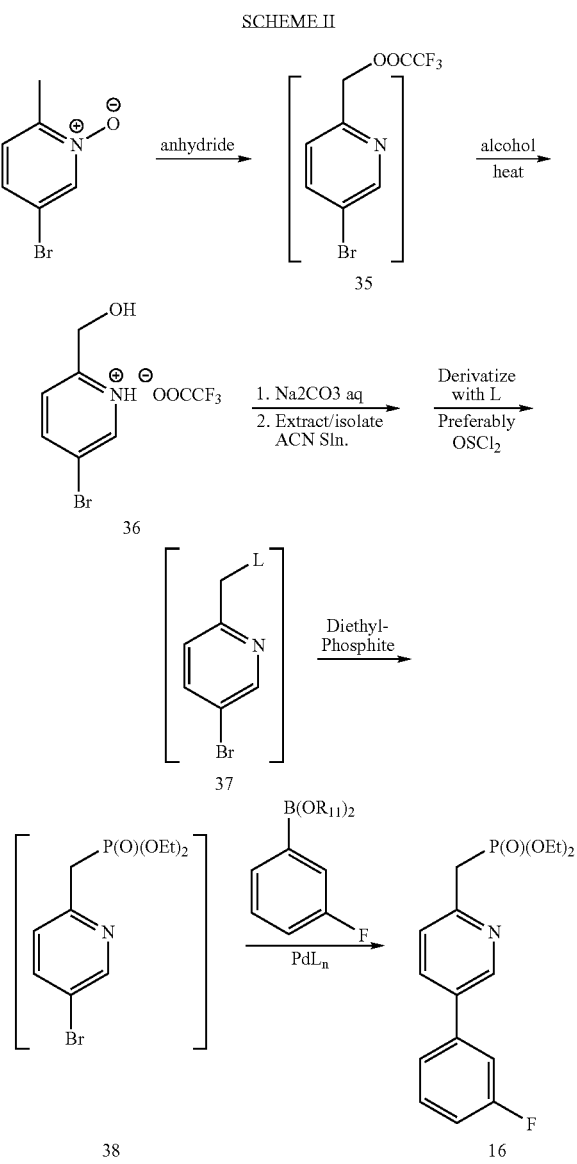

With reference to Scheme II, L is a leaving group selected from halogens, esters, sulfonates and phosphates, $R^9$ is selected from alkyl, aryl heteroaryl and arylalkyl groups having 1 to 10 carbon atoms, and $R^{11}$ is selected from alkyl, aryl heteroaryl and arylalkyl groups having 1 to 10 carbon atoms and hydrogen. As described in the '324 application, in the scheme for preparation of compound 16, compound 36 is converted to compound 37 by first treatment with sodium carbonate to liberate the pyridyl alcohol free base, and the alcohol is subsequently reacted to convert the hydroxyl group to a leaving group (L) which can be displaced by a phosphite reagent to form the corresponding phosphonate ester. Accordingly, as described in the '324 application, preferably compound 37 is prepared by heating a solution of the alcohol intermediate isolated from compound 36 with a reagent that converts the hydroxyl functional group to a leaving group which can be displaced by a diorgano-phosphite compound. Preferably, L is a halogen, preferably Cl, and is preferably prepared by treating the alcohol with a halogenation reagent, for example, $PBr_3$, $PCl_3$, $PCl_5$, and thionyl chloride, preferably thionyl chloride, followed by quenching the reaction with sodium carbonate, and extracting the product into toluene.

Compound 37 contained in the toluene extract is converted to compound 38 by reacting a solution of compound 37 with a diorgano-phosphite in the presence of a strong base, for example, a metal alkyl, for example, lithium alkyl and a metal amide, for example lithium bis(trimethylsilyl) amide.

The conversion of compound 38 to compound 16 is done by reacting compound 38 with boronate, the reaction catalyzed by a palladium catalyst. The catalyst used can be a homogeneous catalyst, for example, a palladium phosphine, for example, palladium tristriphenyl phosphine, and palladium tris-ortho-tolyphosphine, and amine catalysts, for example, bispalladium-trisbipyridine, or a heterogeneous catalyst, for example, palladium supported on carbon black.

The scheme presented in the '345 application for the synthesis of compound 16, a critical intermediate in the preparation of a variety of thrombin receptor antagonists, requires isolation or extraction of intermediates in two of the four steps, and utilizes in one step a powerful base and a water sensitive diorgano-phosphite compound. Moreover, the step shown in Scheme II of reacting unisolated compound 38 with boronate to form compound 16 proved to provide variable results, rendering the process of Scheme II undesirable for use in the preparation of commercial quantities of material.

OBJECTIVES

In view of the foregoing, what is needed is a synthetic scheme useful for preparing compounds critical to the preparation of thrombin receptor antagonists. Particularly needed is a synthetic scheme which utilizes safer materials and provides reaction steps and processes affording practical scale up to a batch size suitable for commercial scale preparation and requires minimal equipment for isolation and purification of intermediates and products and improved product yield. These and other objectives and/or advantages are provided by the present invention.

SUMMARY OF THE INVENTION

In one embodiment, the present invention is a novel, simple process of making dialkyl{[5-(3-fluorophenyl)-pyridine-2-yl]methyl} phosphonate compounds (compounds having the structure of compound 116) which are useful in the synthesis of himbacine analogs that have utility as thrombin receptor antagonist compounds:

Compound 116

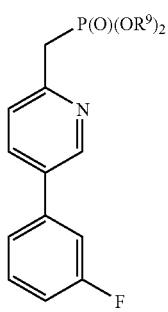

wherein $R^9$ is selected from alkyl, aryl, heteroaryl, and arylalkyl groups having 1 to 10 carbon atoms, the process comprising:

(a) reacting (5-halo-pyridin-2-yl)-methanol of the Formula 137A

Formula 137A

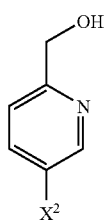

with an $X^1$ halogenating agent, to produce a compound of the formula of compound 137, Compound 137

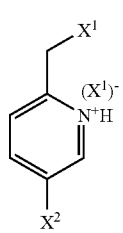

where $X^1$ is the same for each occurrence and is selected from Cl or Br and $X^2$ is selected independently from Cl, Br, or I;

(b) reacting compound 137 with a phosphite compound of the structure of Formula A Formula A

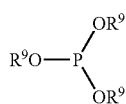

to produce compound 138

COMPOUND 138

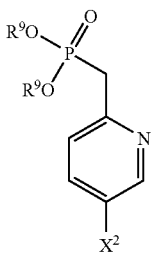

wherein $R^9$ is as defined above;

(c) treating compound 138 with $HX^3$, where $X^3$ is selected from Cl and Br, to precipitate the corresponding hydrohalide salt of Formula 138 A Formula 138 A

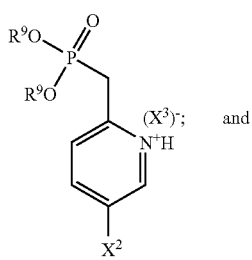

(d) reacting the hydrohalide salt from step "c" with a 3-flurophenylboronate compound of the structure of Formula B Formula B

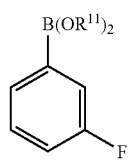

wherein $R^{11}$ is selected independently for each occurrence from alkyl, aryl heteroaryl and arylalkyl groups having 1 to 10 carbon atoms and hydrogen, optionally in the presence of a palladium catalyst to produce compound 116.

Preferably, the halogenating agent used in step "c" is selected from a chlorinating agent (therefore $X^1$ is Cl) or a brominating agent (therefore $X^1$ is Br) selected from $OSCl_2$, $PCl_3$, $PCl_5$, $POCl_3$, $O_2SCl_2$, $(OCCl)_2$, $OSBr_2$, $PBr_3$, $PBr_5$, $POBr_3$, $O_2SBr_2$, $(OCBr)_2$, more preferably the halogenating agent is thionyl chloride (therefore $X^1$ is Cl). Preferably, the phosphite compound used in step "b" is a trialkyl phosphite, more preferably, triethyl phosphite. Preferably the boronate compound used in step "d" is 3-fluoro-phenyl-boronic acid. When a catalyst is used in the reaction of step "d", preferably the catalyst is palladium supported on carbon black. Preferably, a catalyst is used in step "d".

In some embodiments of the present invention, the method of the present invention for the preparation of a compound of the structure of compound 116 is part of a larger reaction scheme for the preparation of a thrombin receptor antagonist having the structure of compound 11, as shown below in Scheme III.

SCHEME III

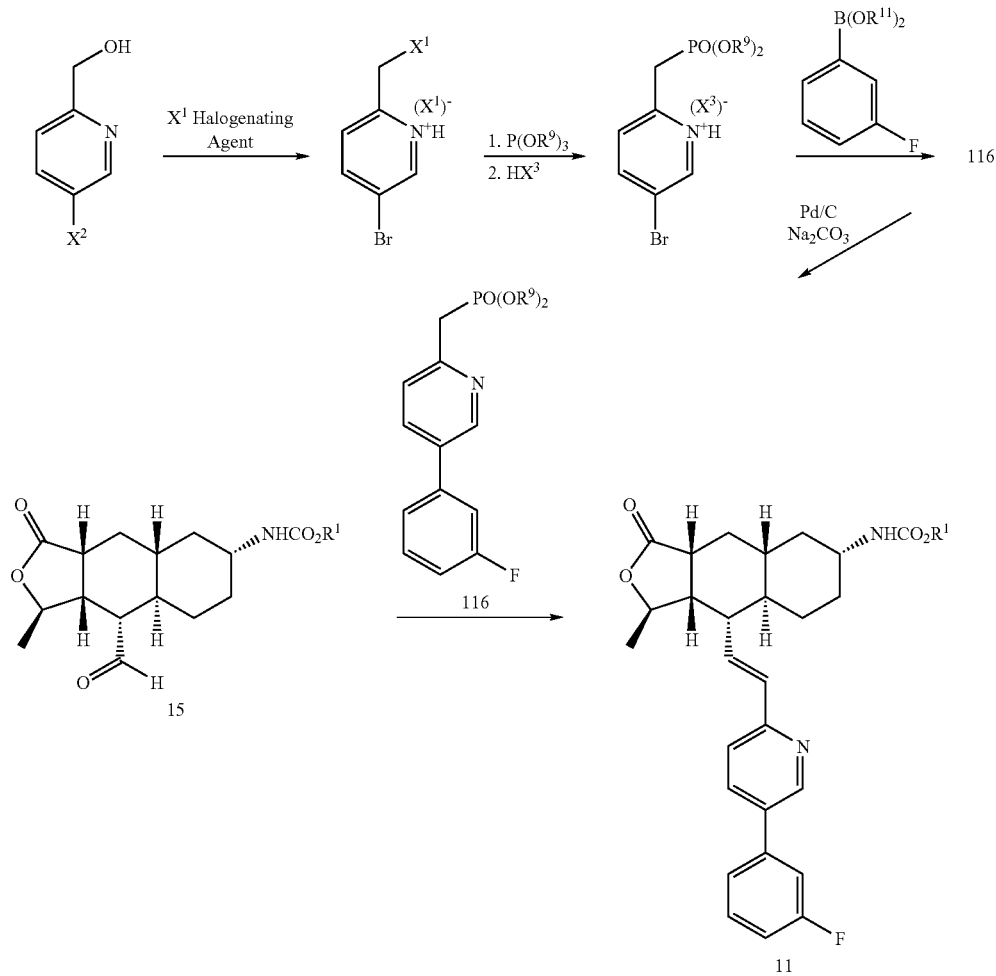

wherein the halogenating agent is selected from a chlorinating agent ($X^1$ is Cl) selected from $OSCl_2$, $PCl_3$, $PCl_5$, $POCl_3$, $O_2SCl_2$, $(OCCl)_2$, and a brominating ($X^1$ is Br) selected from $OSBr_2$, $PBr_3$, $PBr_5$, $POBr_3$, $O_2SBr_2$, $(OCBr)_2$; $X^1$ is the same for each occurrence and is selected, based on the halogenating agent chosen, from Cl or Br; $X^2$ is Cl, Br, or I; $X^3$ is selected from Cl and Br; $R^1$ is a linear, branched or cyclic alkyl, preferably having from 1 to about 4 carbon atoms, more preferably $C_2H_5$—; $R^9$ is selected from alkyl, aryl, heteroaryl, and arylalkyl groups having 1 to 10 carbon atoms; and $R^{11}$ is selected independently for each occurrence from alkyl, aryl heteroaryl and arylalkyl groups having 1 to 10 carbon atoms and hydrogen. In some embodiments, the halogenating agent is preferably thionyl chloride, $X^1$ and $X^3$ are preferably Cl and $X^2$ is preferably Br. In some embodiments R9 is preferably $C_2H_5$—. In some embodiments the phosphite compound used is preferably a trialkyl phosphite, more preferably, triethyl phosphite. Preferably the boronate compound used is 3-fluoro-phenyl-boronic acid.

These and other aspects and advantages of the invention will be apparent from the following description.

DETAILED DESCRIPTION OF THE INVENTION

The following definitions and terms are used herein or are otherwise known to a skilled artisan. Except where stated otherwise, the definitions apply throughout the specification and claims. Chemical names, common names and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Unless otherwise known, stated or shown to be to the contrary, the point of attachment for a multiple term substituent (two or more terms that are combined to identify a single moiety) to a subject structure is through the last named term of the multiple term substituent. For example, a cycloalkylalkyl substituent attaches to a targeted structure through the latter "alkyl" portion of the substituent (e.g., structure-alkyl-cycloalkyl).

The identity of each variable appearing more than once in a formula may be independently selected from the definition for that variable, unless otherwise indicated.

Unless stated, shown or otherwise known to be the contrary, all atoms illustrated in chemical formulas for covalent compounds possess normal valencies. Thus, hydrogen atoms, double bonds, triple bonds and ring structures need not be expressly depicted in a general chemical formula.

Double bonds, where appropriate, may be represented by the presence of parentheses around an atom in a chemical formula. For example, a carbonyl functionality, —CO—, may also be represented in a chemical formula by —C(O)—, or —C(=O)—. One skilled in the art will be able to determine the presence or absence of double (and triple bonds) in a covalently-bonded molecule. For instance, it is readily recognized that a carboxyl functionality may be equivalently represented by —COOH, —C(O)OH, —C(=O)OH or —CO$_2$H.

The term "heteroatom," as used herein, means a nitrogen, sulfur or oxygen atom. Multiple heteroatoms in the same group may be the same or different.

As used herein, the term "alkyl" means an aliphatic hydrocarbon group that can be straight or branched and comprises 1 to about 24 carbon atoms in the chain. Preferred alkyl groups comprise 1 to about 15 carbon atoms in the chain. More preferred alkyl groups comprise 1 to about 6 carbon atoms in the chain. "Lower alkyl" means alkyl groups of 1 to 6 carbon atoms in the chain. "Branched" means that one or more lower alkyl groups such as methyl, ethyl or propyl, are attached to a linear alkyl chain. The alkyl can be substituted by one or more substituents independently selected from the group consisting of halo, aryl, cycloalkyl, cyano, hydroxy, alkoxy, alkylthio, amino, —NH(alkyl), —NH(cycloalkyl), —N(alkyl)$_2$ (which alkyls can be the same or different), carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkoxy" means an alkyl-O— group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen.

The term "cycloalkyl" as used herein, means an unsubstituted or substituted, saturated, stable, non-aromatic, chemically-feasible carbocyclic ring having preferably from three to fifteen carbon atoms, more preferably, from three to eight carbon atoms. The cycloalkyl carbon ring radical is saturated and may be fused, for example, benzofused, with one to two cycloalkyl, aromatic, heterocyclic or heteroaromatic rings. The cycloalkyl may be attached at any endocyclic carbon atom that results in a stable structure. Preferred carbocyclic rings have from five to six carbons. Examples of cycloalkyl radicals include cyclopropyl, cyclobutyl, cyclopentyl, cyclohexyl, cycloheptyl, or the like.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 10 carbon atoms in the chain; and more preferably about 2 to about 6 carbon atoms in the chain. Branched means that one or more lower alkyl groups such as methyl, ethyl or propyl, are attached to a linear alkynyl chain. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, aryl and cycloalkyl.

The term "aryl," as used herein, means a substituted or unsubstituted, aromatic, mono- or bicyclic, chemically-feasible carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, tolyl, xylyl, cumenyl, naphthyl, tetrahydronaphthyl, indanyl, indenyl, or the like. If desired, the carbocyclic moiety can be substituted with from one to five, preferably, one to three, moieties, such as mono- through pentahalo, alkyl, trifluoromethyl, phenyl, hydroxy, alkoxy, phenoxy, amino, monoalkylamino, dialkylamino, or the like.

"Heteroaryl" means a monocyclic or multicyclic aromatic ring system of about 5 to about 14 ring atoms, preferably about 5 to about 10 ring atoms, in which one or more of the atoms in the ring system is/are atoms other than carbon, for example nitrogen, oxygen or sulfur. Mono- and polycyclic (e.g., bicyclic) heteroaryl groups can be unsubstituted or substituted with a plurality of substituents, preferably, one to five substituents, more preferably, one, two or three substituents (e.g., mono- through pentahalo, alkyl, trifluoromethyl, phenyl, hydroxy, alkoxy, phenoxy, amino, monoalkylamino, dialkylamino, or the like). Typically, a heteroaryl group represents a chemically-feasible cyclic group of five or six atoms, or a chemically-feasible bicyclic group of nine or ten atoms, at least one of which is carbon, and having at least one oxygen, sulfur or nitrogen atom interrupting a carbocyclic ring having a sufficient number of pi ($\pi$) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "heterocyclic ring" or "heterocycle," as used herein, means an unsubstituted or substituted, saturated, unsaturated or aromatic, chemically-feasible ring, comprised of carbon atoms and one or more heteroatoms in the ring. Heterocyclic rings may be monocyclic or polycyclic. Monocyclic rings preferably contain from three to eight atoms in the ring structure, more preferably, five to seven atoms. Polycyclic ring systems consisting of two rings preferably contain from six to sixteen atoms, most preferably, ten to twelve atoms. Polycyclic ring systems consisting of three rings contain preferably from thirteen to seventeen atoms, more preferably, fourteen or fifteen atoms. Each heterocyclic ring has at least one heteroatom. Unless otherwise stated, the heteroatoms may each be independently selected from the group consisting of nitrogen, sulfur and oxygen atoms.

The terms "Hal," "halo," "halogen" and "halide," as used herein, mean a chloro, bromo, fluoro or iodo atom radical. Chlorides, bromides and fluorides are preferred halides.

The term "carbonate", as used herein, is understood to include bicarbonates.

The term "isomer", as used herein, is understood to mean one of two or more molecules having the same number and kind of atoms and hence the same molecular weight, but differing in respect to the arrangement or configuration of the atoms.

The term "epimerizing", as used herein, is understood to mean converting from one isomer to another, wherein it is the relative position of an attached H that differs between the two isomers.

The term "precipitate", as used herein, is understood to mean to fall out of solution as a solid. Precipitation applies equally to the formation of an insoluble salt "in situ", or changing the solubility properties of a solvent. Examples of changing the solubility properties of a solvent include cooling the solution and the addition of a sufficient amount of an "anti-solvent" to a solution such that precipitated compound has reduced solubility in the combined solvents.

The term "dynamic resolution", as used herein, is understood to mean a process in which a conversion from a first isomer to a second isomer of the same compound in a solution is thermodynamically driven by the depletion of the second isomer from the solution by precipitation of the second isomer.

The following abbreviations are defined: EtOH is ethanol; Me is methyl; Et is ethyl; Bu is butyl; n-Bu is normal-butyl, t-Bu is tert-butyl, OAc is acetate; KOt-Bu is potassium tert-butoxide; NBS is N-bromo succinimide; NMP is 1-methyl-2-pyrrolidinone; DMAP is 4-dimethylaminopyridine; THF is tetrahydrofuran; DBU is 1,8-diazabicyclo[5,4,0]undec-7-ene; DMA is N,N-dimethylacetamide; n-BU$_4$NBr is tetrabutylammonium bromide; n-Bu$_4$NOH is tetrabutylammonium hydroxide, n-Bu$_4$NH$_2$SO$_4$ is tetrabutylammonium hydrogen sulfate, and "equiv." or "eq." means equivalents.

The term "n", as it is used herein, is understood to be an integer having a value that is inclusive of the range recited thereafter. Thus "n is between 0 and 4" and "n ranges 0-4" both mean that n may have any of the values 0, 1, 2, 3 or 4.

As mentioned above, copending U.S. patent application Ser. No. 11/331,324 (herein, "the '324 application") describes the synthesis of compounds of the structure of compound 11 which have promising activity as thrombin receptor inhibitors.

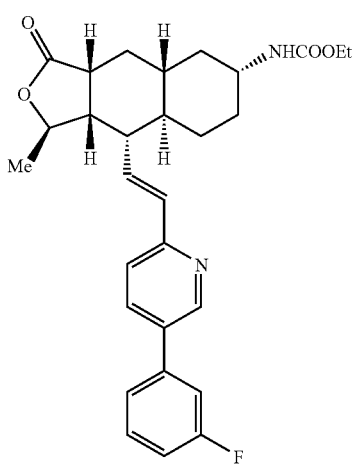

11

As illustrated below in Schemes IV and V, the '324 application describes in detail the synthesis of compound 11 and related compounds, which synthesis is incorporated herein by reference.

SCHEME IV - Nitro-Ester Route

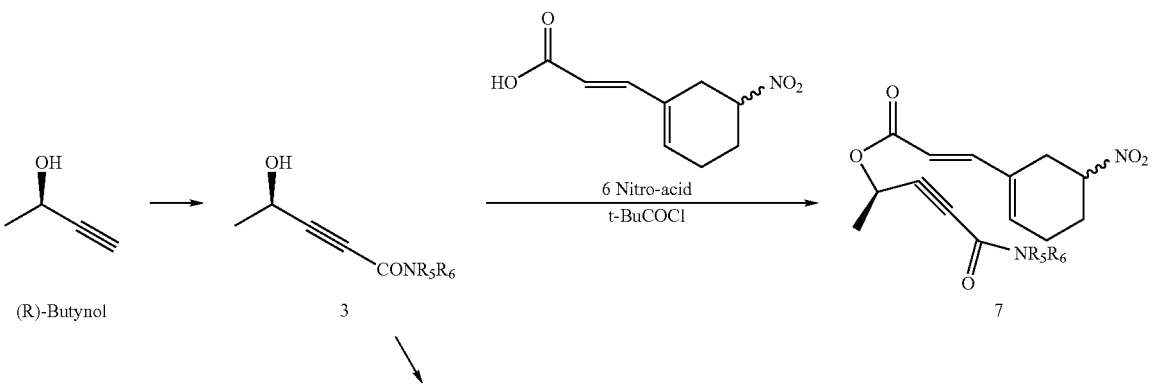

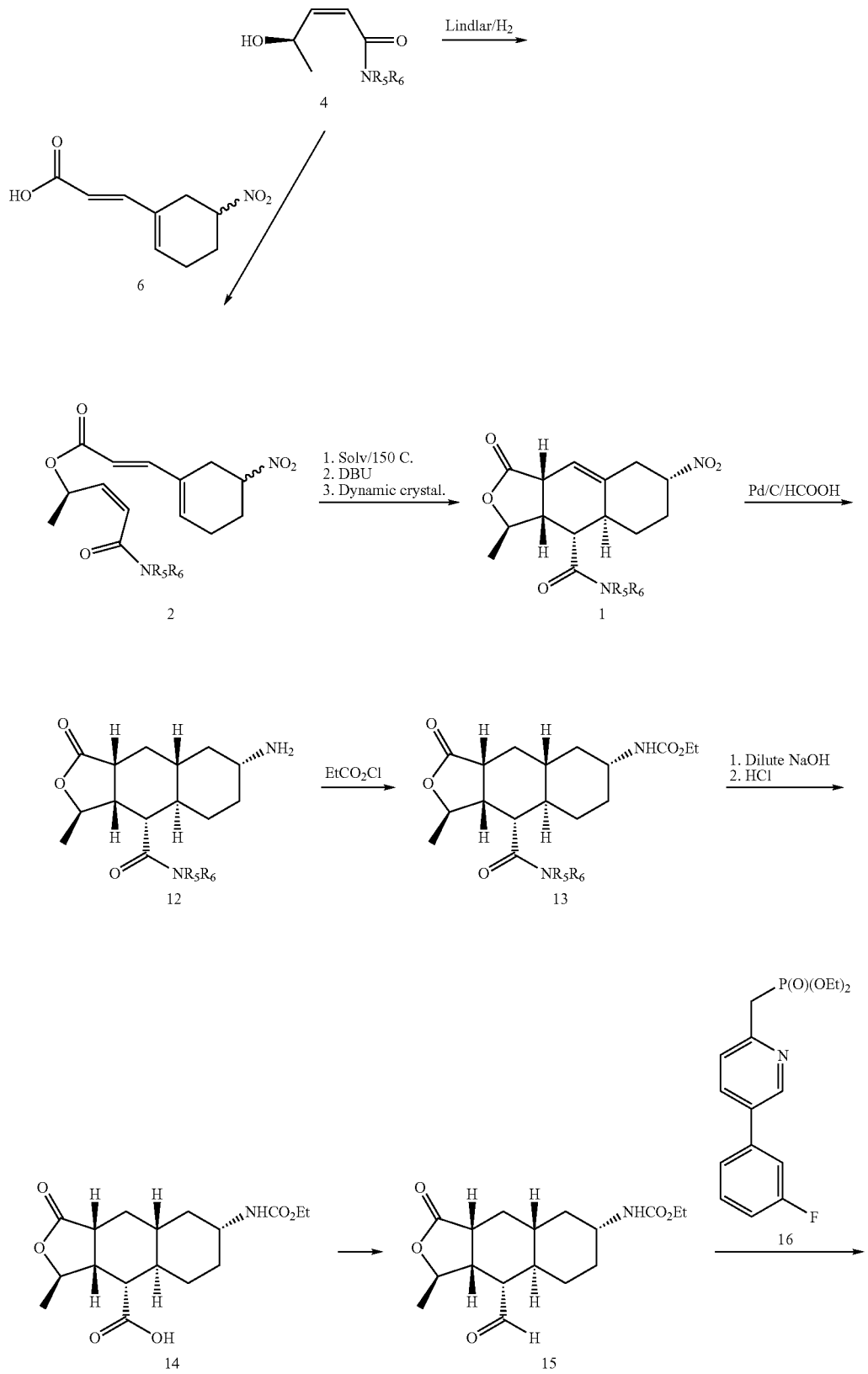

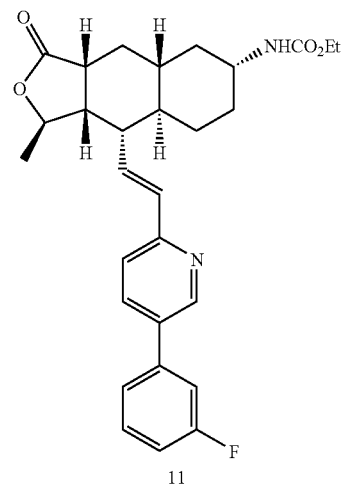
11
SCHEME V - Nitro-Oxazole Route:
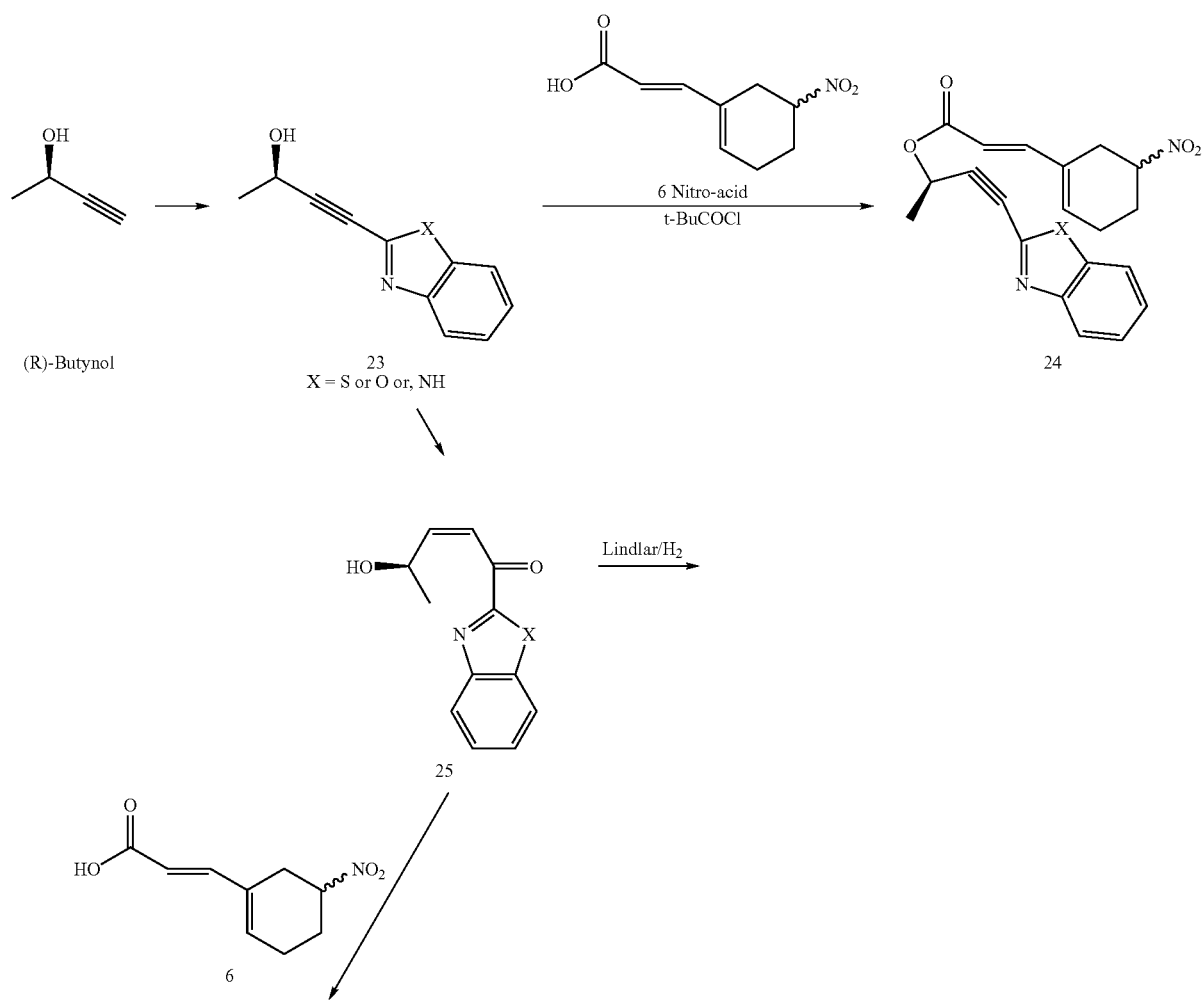

-continued
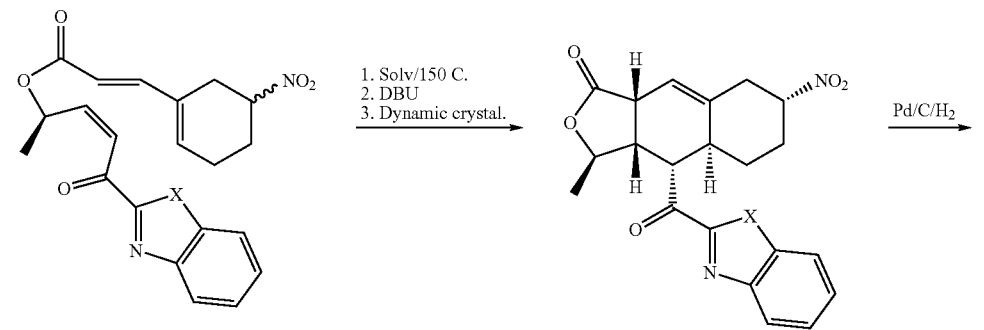
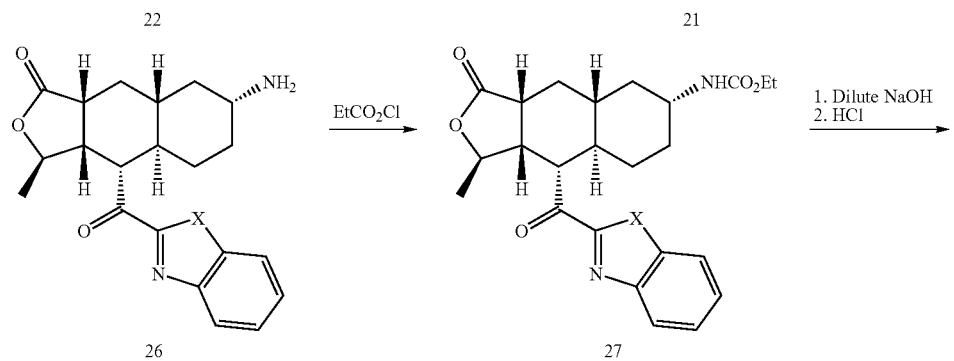
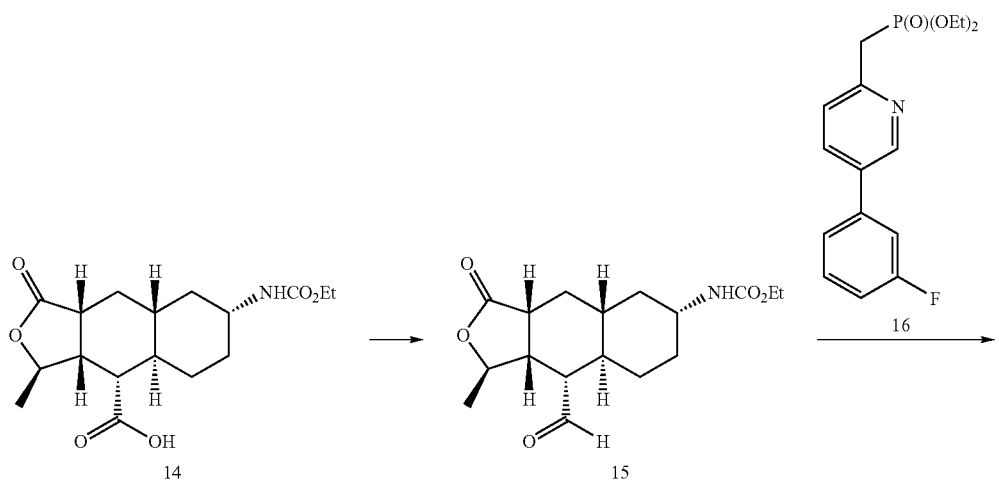
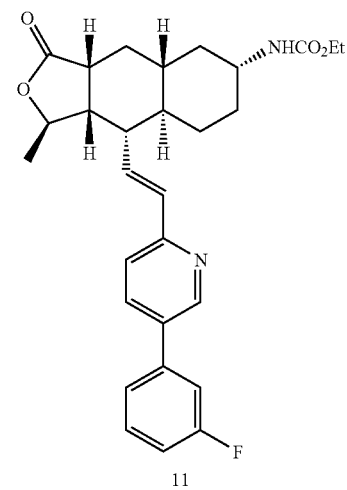

A critical intermediate in the synthesis of compound 11 are compounds having the structure of compound 16 and related phoshonate esters (herein, sometimes referred to for convenience as the compounds having the structure of compound 116). The inventors have surprisingly discovered a process for the synthesis of the compounds having the structure of compound 116 which uses less active reagents and simplifies unit operations in each synthetic step over a process for the preparation of compounds having the structure of compound 116 described in the '324 application. In particular, improvements in yield, specificity, and product purity are realized by isolation of 5-halo-pyridin-2-yl-methyl phosphonate ester (139), and by selection of a triorganophosphite phosphonating agent in the conversion of compound 137 to compound 138. Moreover, utilizing these process steps, the current invention process results in a greater overall yield of compounds having the structure of compound 116 based on the starting pyridyl alcohol, 75% overall yield for the process of the present invention compared with an overall yield of 60% for the process described in the '324 application.

The overall reaction scheme of the present invention is schematically depicted in Scheme VI.

L is Br). As will be appreciated, the L-derivatizing reagent can also be a moiety which converts the alcohol functional group to any leaving group which can be displaced by the phosphonating agent (triorgano-phosphite) used to covert compound 137D to compound 138D, for example a sulfonylester (provided by, for example, benzensulfonyl chloride L-derivatizing reagent), a sulfonate ester, and the L-derivatizing reagents described in the copending '324 application, (incorporated herein by reference).

Although all steps of Reaction Scheme VI can be carried out individually, and the intermediate prepared in each phase isolated, it is advantageous in the present reaction scheme to utilize intermediate compound 137 "in situ" in the reaction medium obtained after workup for use in the next step, the conversion from the halide to the phosphonate (compound 138).

Each step of reaction Scheme VI will be discussed next.

The first step of the process of the invention is conversion of a pyridyl hydroxyalkyl to the correspondind phosphonoalkyl. This is illustrated in Scheme VI as the first step, conversion of compound 136 to compounds of the structure 138. In the first step of Scheme VI, the alcohol functional group of

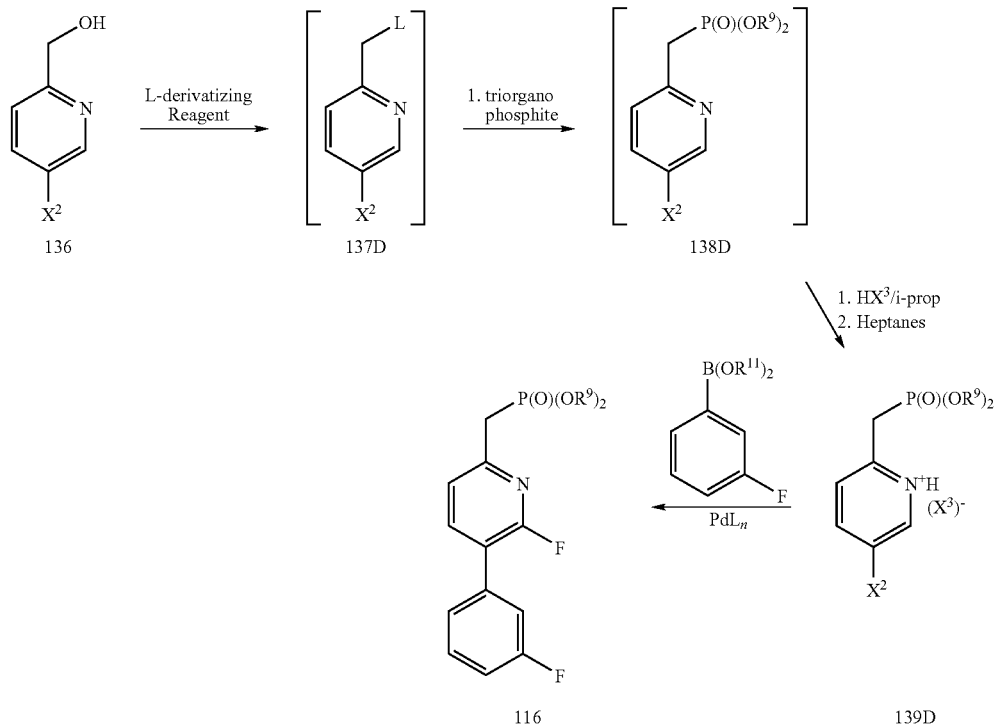

SCHEME VI wherein $R^9$ is selected from alkyl, aryl heteroaryl and arylalkyl groups having 1 to 10 carbon atoms, and $R^{11}$ is selected independently for each occurrence from alkyl, aryl heteroaryl and arylalkyl groups having 1 to 10 carbon atoms and hydrogen, $X^2$ is Cl, Br, or I; $X^3$ is selected from Cl and Br; and $PdL_n$ is a supported palladium metal catalyst or a soluble heterogeneous palladium catalyst. The L-derivatizing reagent can be a halogenating agent (thus L is a halogen), for example, a chlorinating agent, for example, $OSCl_2$, $PCl_3$, $PCl_5$, $POCl_3$, $O_2SCl_2$, $(OCCl)_2$ (thus L is Cl), and a brominating agent, for example $OSBr_2$, $PBr_3$, $PBr_5$, $POBr_3$, $O_2SBr_2$, $(OCBr)_2$ (thus, [(5-(halo)-2-hydroxymethyl]-pyridine, where "halo" is selected from bromine, chlorine and iodine, is reacted in solution with an L-derivatizing reagent, as mentioned above, for example, a chlorinating agent, for example $OSCl_2$, $PCl_3$, $PCl_5$, $POCl_3$, $O_2SCl_2$, $(OCCl)_2$ (thus L is Cl), a brominating agent, for example $OSBr_2$, $PBr_3$, $PBr_5$, $POBr_3$, $O_2SBr_2$, $(OCBr)_2$ (thus, L is Br), and a sulfonating agent, thus L is a sulfonyl ester, to provide the corresponding 5-Bromo-2-(L) methyl-pyridine, preferably, 5-Bromo-2-(halo)methyl-pyridine, where "halo" is preferably Cl, Br, and I. Although any of the above-mentioned L-derivatizing agents are suitable for the process of the invention, it is preferable to use thionyl chloride. It will be appreciated that other L-derivatizing agents not specifically mentioned herein may also be used in the process of the present invention. Any suitable solvent system may be employed, preferably a solvent system comprising non-protic solvents of moderate polarity, for example a mixture of toluene and acetonitrile (MeCN). It is preferable to carry out the reaction in a temperature range of from about 0° C. to about 70° C., more preferably from about 20° C. to about 50° C., more preferably at about 45° C. Preferably the initial concentration of the alcohol substrate is from about 0.5 M to about 0.9 M. Preferably, the chlorinating agent is used at least in a 1.5-fold excess based on the alcohol substrate.

It is preferable to run the reaction until the alcohol has been completely consumed. The reaction can be monitored for complete conversion of the alcohol, for example, by HPLC or gas chromatographic techniques. At the end of the reaction, optionally the reaction mixture is quenched with an aqueous base. It is particularly preferred to quench the reaction when it is being carried out on a large scale. When a quench step is included in the reaction, preferably, the reaction is quenched using a potassium carbonate solution. Following completion of the reaction, the organic layer of the reaction mixture is separated, washed and concentrated.

Thus obtained, the concentrate is charged into a suitable apparatus and combined with triorgano-phosphite compound having the structure of Formula A, wherein $R^9$ is selected independently for each occurrence from alkyl, aryl heteroaryl and arylalkyl groups having 1 to 10 carbon atoms.

Formula A

Preferably, $R^9$ is the same for all occurrences and is alkyl, more preferably linear alkyl, more preferably ethyl.

The reaction mixture is heated and maintained at a temperature to drive the reaction, preferably to a temperature of from about 130° C. to about 150° C. After a sufficient period of maintaining the reaction mixture at a suitable temperatrue, preferably until complete conversion of the methyl-L derivatized substrate (the compound 137D for example, when a chlorinating L-derivatizing reagent is employed, a methylchloride substrate) the reaction mixture is cooled and treated with hydrochloric acid to convert the phosphonate (compound 138D) into the corresponding hydrochloride salt (compound 139D). Preferably, the temperature of the reaction mixture is maintained at less than about 20° C. during this treatment. Although HCl treatment can be carried out using any conventional means, for example, by bubbling HCl gas through the reaction mixture, or treating the mixture with an HCl solution, it is convenient to treat the reaction mixture by stirring it with an HCl solution, preferably an HCl/isopropanol solution.

After the salt is formed, it begins to precipitate from the reaction mixture. Heptanes are added to complete the salt precipitation and improve the yield of salt recovered from the reaction mixture. It is preferred to keep the reaction mixture at a temperature of less than about 20° C. during this addition. The phosphonate hydrohalide salt (compound 139D) is then recovered from the reaction mixture by vacuum filtration, washed and vacuum dried for use in the synthesis of compound 116.

In the last step of Scheme VI, compound 116 is synthesized from the phosphonate hydrochloride salt by reacting it with a 3-fluorophenylboronate of the structure of the compound of Formula B:

Formula B where $R^{11}$ is selected independently for each occurrence from alkyl, aryl heteroaryl and arylalkyl groups having 1 to 10 carbon atoms and hydrogen.

Although it will be appreciated that any 3-fluorophenyl boronate can be reacted with the (5-halo-pyrid-2-yl)-methylphosphonate salt compound (139D), it is preferred to use 3-fluoroboronic acid (thus $R^{11}$ for each occurrence is H). It is preferred to carry this reaction out in a two phase reaction medium, one aqueous and one organic, preferably isobutyl acetate. Accordingly, the reaction is carried out by providing an aqueous boronic acid solution/slurried with a supported palladium catalyst, for example, palladium supported on carbon black, for example, Degussa 5% Pd/C type E 105 CA/W. Conversion of the phosphonate hydrochloride salt (compound 139D) can be followed by HPLC assay. It is preferred to maintain reaction conditions until the HPLC analysis indicates complete conversion of the starting phosphonate. It is preferred to maintain the reaction mixture at a temperature of from about 70° C. to about 80° C. during the reaction. It is preferred to initiate the reaction with the starting phosphonate (compound 139D) present at a concentration of about 0.5 M to about 1.0 M, and use at least a 1.3-fold excess of the boronate reagent. Workup of the reaction mixture includes removing excess boronic acid by adjusting the mixture to a basic pH, preferably a pH of from about pH 11 to about pH 13, separating the organic layer by splitting, and removing process impurities by washing the batch with a 2% aqueous NaCl solution, and concentrating the organic layer. During workup, it is preferred to maintain the reaction mixture at a temperature of from about 20° C. to about 30° C. Product, compound 116, is obtained by anti-solvent precipitation, for example, by treating the organic phase with a sufficient volume of heptanes until the product precipitates from solution.

With reference to Scheme IV, it will be appreciated that the intermediate compounds of Formula 116 can be prepared by reacting intermediate compounds of Formula 139d with other organometallic reactants in place of boronates, for example, but not limited to: fluoroaryl-alkylboranes; fluoroaryl-haloboranes; fluoroaryl- zinc, -aluminium, -magnesium, and -tin reagents, and other organometallic reagents represented by formula

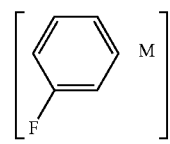

where "M" is an organometallic reagent capable of displacing the $X^2$ halogen of compound 138 with a 3-fluoroaryl moiety.

The starting alcohol, 5-bromo-2-hydroxymethyl-pyridine, compound 136, may be prepared from 5-bromo-2methyl-pyridine-N-oxide. This synthesis is disclosed in detail in the copending '324 application, which is incorporated herein in its entirety by reference. It will be appreciated that the present invention process can be carried out using variously substituted hydroxymethyl pyridines, as well as 5-bromo-2hydroxymethyl-pyridine obtained by any other means.

There follows an example preparation of [5-(3-Fluorophenyl)-pyridin-2-ylmethyl]-phosphonic acid diethyl ester (compound 16) which illustrates, but in no way limits, the present invention.

EXAMPLE

The following solvents and reagents may be referred to by their abbreviations in parenthesis:
ethyl acetates: EtOAc
methanol: MeOH
isopropanol: IPA
tertiarybutyl-methyl ether: TBMEsodium bistrimethylsilylamide: NaHMDS
triethyl amine: TEA
trifluoro acetic acid: TFA
tertiary-butoxycarbonyl: t-BOC
tetrahydrofuran: THF
lithium bis(trimethylsilyl)amide: LiHMDS
mole: mol.
HPLC—high pressure liquid chromatography Example 1

Preparation of [5-(3-Fluoro-phenyl)-pyridin-2-ylmethyl]-phosphonic acid diethyl ester

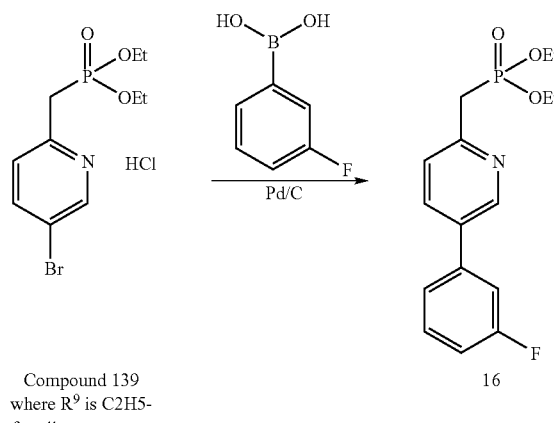

Compound 139
where $R^9$ is C2H5-
for all occurrences

To a reaction vessel was charged (100 g, 0.29 mol) of phosphonate compound 139 (where $R^9$ is ethyl- for all occurrences), 5% Pd/C 50% wet (5.0 g), 3-fluorophenylboronic acid (61 g; 0.44 mol) and sodium carbonate (100 g; 0.94 mol). 600 ml of iso-butyl acetate was charged and the mixture agitated. 400 ml of water was charged, and the agitated mixture was heated to 70-80° C. for at least 3 h at which time an HPLC assay indicated complete reaction. Upon completion, the reaction mixture was cooled to 25° C. and filtered to remove the Pd/C catalyst. The catalyst cake was washed with 200 ml iso-butyl acetate (combined with the filtrate/batch) and 100 ml water (waste). 25% sodium hydroxide solution was used to adjust batch to pH 11-13. During the process the reaction mixture was maintained at a temperature of from 20° C. to 30° C. The organic layer was separated and washed with 500 ml water with agitation. A 25% sodium hydroxide solution was used to adjust the pH of the batch to a pH value of from pH 11 to pH13. Throughout the was the temperature was maintained at a value of from about 20° C. to about 30° C.

After washing the layers were separated and the organic layer was washed with 300 ml of 2% sodium chloride solution with 10-15 minutes with agitation. The layers were separated and an HPLC assay of the organic layer indicated impurities were reduced to a desirable level. Darco (10 g) was added to the organic layer. The resultant slurry was agitated for 1 hour, and then filtered to remove the de-coloring agent. The filter cake was washed with 200 ml iso-butyl acetate (combined with the filtrate/batch) and the batch was concentrated under reduced pressure to about 200 ml at from 40° C. to 50° C., then cooled to a temperature of from 15° C. to 25° C. Heptanes (1000 ml) were charged into the cold concentrate over 2.5-3 hr, maintaining the temperature at from about 15° C. to 25° C. The mixture was cooled to a temperature of from −15° C. to −5° C. over 3 hr and agitated at the same temperature for 1 hr. The crystalline solid was filtered, washed with 200 ml heptanes, and dried overnight under vacuum at a temperature of from about 25° C. to 35° C. to provide 70.37 g (75%). Mp 61-63° C. $^1$H NMR (CDCl$_3$) δ 1.3 (t, J=7.05 Hz, 6H), 3.47 (d, J=22.02 Hz, 2H), 4.12 (q, J=7.08 Hz, 4H), 7.10 (ddd, J=8.42, 2.55, 0.88, Hz, 1H), 7.28 (ddd, J=9.85, 2.36, 1.80 Hz, 1H), 7.36 (dt, J=7.86, 1.27, Hz, 1H), 7.46 (m, 1H), 7.83 (ddd, J=8.1, 2.2, 0.32 Hz, 1H), 8.76 (d, J=2.38, 1H).

Example 1A

Preparation of [(5-Bromo-Pyridin-2-ylMethyl)-Phosphonic Acid Diethyl Ester] Hydrochloride Compound 139
where $R^9$ is C2H5—
for all occurrences Into a solution of 5-bromo-2-hydroxymethyl-pyridine (BHMP, 50.0 g, 266 mmol) in toluene (100 mL) and MeCN (150 mL) was added thionyl chloride (35.0 mL, 57.1 g, 479 mmol). This reaction mixture was stirred at 45° C. for 4 hours.

Toluene (250 mL) was added to the reaction mixture and the reaction mixture was cooled to 0° C. The reaction was quenched with 20% potassium carbonate solution (450 ml), keeping the temperature below 30° C. The reaction mixture was stirred for 10 min and the layers were partitioned. The organic layer was washed once with water (100 mL) and the organic layer was concentrated under reduced pressure to a volume of about 200 mL. The concentrated crude solution was transferred to a distillation apparatus. At room temperature, triethyl phosphite (200 mL, 1144 mmol) was added to the crude concentrated solution and the reaction mixture was heated to 145° C. until reaction was completed. Distillate driven off of the reaction mixture during the heating period was collected (~200 mL). After 12 hours of heating the reaction mixture was cooled to 0° C. A solution of 5-6N HCl in isopropanol (150 mL) was slowly added to the cooled reaction mixture over a period of 1 hour, keeping the internal temperature below 5° C. Heptanes (350 mL) were then added to the mixture over 1 hours and the resultant slurry was stirred for another hour. The solid product was collected by vacuum filtration, washed with 10% IPA/heptanes and dried under vacuum at room temperature to provide 81 g of product (89%). Mp. 118-120° C. $^1$H NMR (400 MHz, CDCl$_3$) δ 1.29 (t, J=7.05 Hz, 6H), 3.88 (d, J=22.3 Hz, 2H), 4.19 (m, 4H), 7.88 (dd, J=8.57 Hz, 1H), 8.34 (dd, J=8.55, 2.18 Hz, 1H), 8.71 (s, 1H).

Preparation of Starting Material:
5-bromo-2-hydroxymethylpyridine

The starting alcohol (5-bromo-2hydroxymethylpyridine) used above in Example 1 was prepared in two steps.

Step I

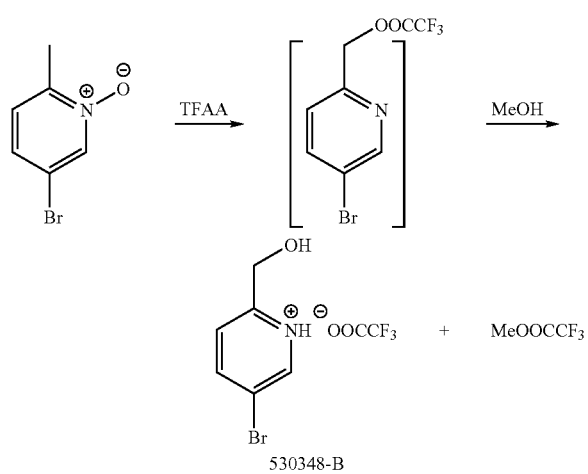

To a solution of 5-bromo-2-methylpyridine N-oxide (10.0 g, 5.32 mmol) in EtOAc (50.0 ml) at 0° C. was added dropwise trifluoroacetic anhydride (9.8 ml, 6.92 mmol.) while keeping the temperature below 50° C. After the completion of the addition, the mixture was heated to a temperature of from 75° C. to 80° C. and stirred for at least 1 h. An HPLC assay of the mixture indicated the reaction was complete when 5-bromo-2-methylpyridine N-oxide was present a less than 5% of its initial value.

Upon completion, the mixture was cooled below 50° C. and MeOH (10.0 ml) was added. The mixture was heated for at least 1 h at 50° C. The solution was concentrated under vacuum and MeOH was removed by displacement with EtOAc (40.0 ml) and concentrated to a volume of 30 ml. To the concentrate was added toluene (20.0 ml) and the solution cooled to −10° C. over 2 h. The crystalline solid was filtered and washed with cold toluene and dried overnight under vacuum at 35° C. to provide 10.1 g (63%) of product. Mp 89-92° C. $^1$H NMR (DMSO-d$_6$) δ 4.56 (s, 2H), 7.49 (d, 1H), 8.1 (dd, J=2.3, 2.3 Hz, 1H), 8.64 (d, J=2.1Hz, 1H).

Step II

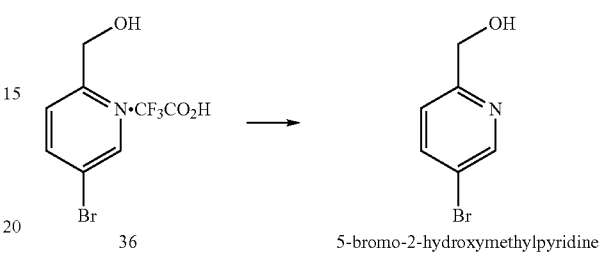

A slurry of compound 36 (10.0 g, 33.1 mmol) in TBME (100 ml) was treated with 20% potassium carbonate (20 ml) solution and stirred at room temperature for 1 h. The layers were separated and the organic layer was washed with water. The solution thus obtained was concentrated to ~10 mL volume and 20 mL heptanes was added at 45-50 C. Solution was cooled to 20-25 C and additional 20 mL heptanes was charged. Reaction was agitated at 20-25 C for 2 hours and filtered. Product was dried overnight under vacuum at 15-25 C to give 5.0 g (80%) of product. $^1$H NMR (CDCl$_3$) δ 3.36 (bs, Hz, 1 —OH), 4.75 (d, J=9.07 Hz, 2H), 7.21 (d, J=8.31 Hz, 1H), 7.83 (d, J=8.28 Hz, 1H), 8.64 (d, J=1.89 Hz, 1H).

The above description of the invention is intended to be illustrative and not limiting. Various changes or modifications in the embodiments described herein may occur to those skilled in the art. These changes can be made without departing from the scope or spirit of the invention

What is claimed is:
1. A process for making a compound having the structure of compound 11:

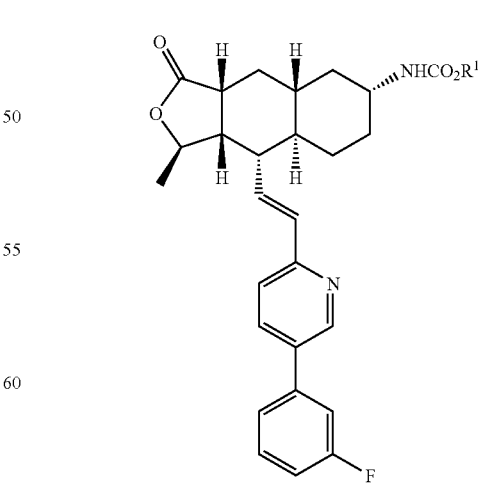

wherein R1 is an alkyl group of from 1 to about 4 carbon atoms, the process comprising:

(a) reacting (5-halo-pyridin-2-yl)-methanol of the Formula 137A

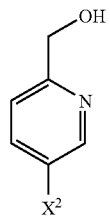

Formula 137A where $X^2$ is selected independently from Cl, Br, or I;
with an $X^1$ halogenating agent, to produce a compound of the formula of compound 137,

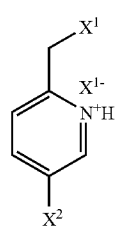

Compound 137 where $X^1$ is the same for each occurrence and is selected from Cl or Br and $X^2$ is as defined above;
(b) reacting compound 137 with a phosphite compound of the structure of Formula A:

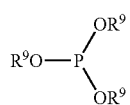

Formula A wherein $R^9$ is selected from alkyl, aryl, heteroaryl, and arylalkyl groups having 1 to 10 carbon atoms, to produce compound 138:

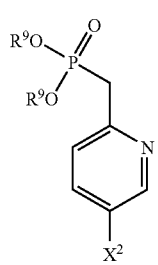

COMPOUND 138 wherein $R^9$ is as defined above;

(c) treating compound 138 with $HX^3$, where $X^3$ is selected from Cl and Br, to precipitate the corresponding hydrohalide salt of Formula 138 A

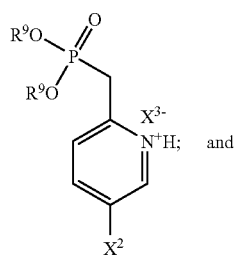

Formula 138 A (d) reacting the hydrohalide salt from step "c" with a 3-flurophenylboronate compound of the structure of Formula B

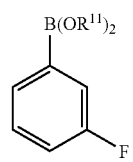

Formula B wherein $R^{11}$ is selected independently for each occurrence from alkyl, aryl heteroaryl and arylalkyl groups having 1 to 10 carbon atoms and hydrogen, optionally in the presence of a palladium catalyst to produce compound 116.

2. A process for making a compound having the structure of compound 11:

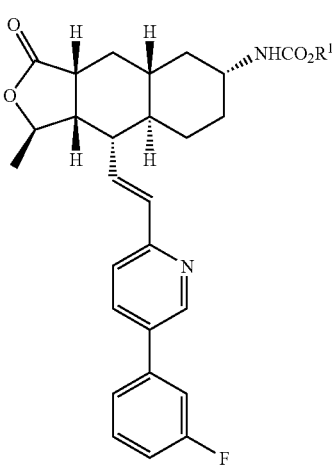

11 wherein R1 is an alkyl group of from 1 to about 4 carbon atoms, the process comprising:
(a) reacting (5-Bromo-2-methoxy-pyridine) with a chlorinating agent selected from $OSCl_2$, $PCl_3$, $PCl_5$, to produce a compound of the formula of compound 137;

Compound 137

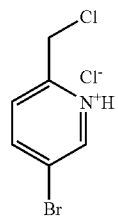

(b) reacting compound 137 with a phosphite compound of the structure of Formula A Formula A

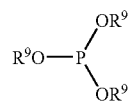

to produce compound 138

COMPOUND 138

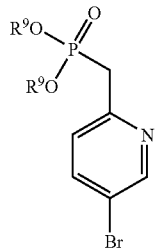

wherein $R^9$ is separately selected for each occurrence from alkyl, aryl, heteroaryl, and arylalkyl groups having 1 to 10 carbon atoms;

(c) treating compound 138 with HCl to obtain the corresponding hydrochloride salt;

(d) reacting the hydrochloride salt from step "c" with 3-flurophenylboronic acid, optionally in the presence of a palladium catalyst to produce compound having the structure of compound 116, Compound 116

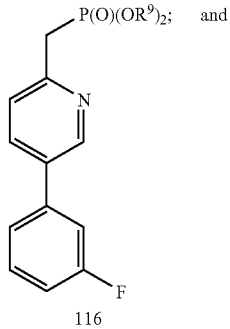

(e) reacting the compound 116 formed in step "d" with a compound of the structure of compound 15, Compound 15

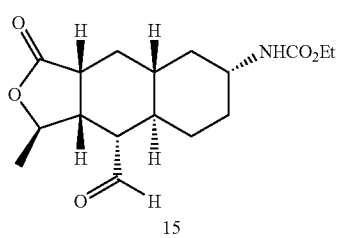

to yield compound 11.

3. The process of claim 2 wherein the phosphite compound used in step "b" is a trialkyl phosphate.

4. The process of claim 2 wherein the phosphite used in step "b" is triethyl phosphite.

5. The process of claim 1 wherein said palladium catalyst is palladium metal supported on carbon black.

6. The process of claim 1 wherein said palladium catalyst is a soluble palladium catalyst.

7. The process of claim 1 wherein the phosphite used in step "b" is triethyl phosphite.

8. The process of claim 2 wherein said palladium catalyst is selected from palladium metal supported on carbon black and a soluble palladium catalyst.

9. The process of claim 3 wherein said palladium catalyst is selected from palladium metal supported on carbon black and a soluble palladium catalyst.

10. The process of claim 4 wherein said palladium catalyst is selected from palladium metal supported on carbon black and a soluble palladium catalyst.

* * * * *